(12) United States Patent
O'Neal et al.

(10) Patent No.: US 7,632,782 B2
(45) Date of Patent: Dec. 15, 2009

(54) SYNERGISTICALLY ACTING HERBICIDAL MIXTURES

(75) Inventors: William B. O'Neal, Chapel Hill, NC (US); Elmar Kibler, Haßloch (DE); Matthias Witschel, Bad Dürkheim (DE); Herve R. Vantieghem, Basking Ridge, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 469 days.

(21) Appl. No.: 10/519,978

(22) PCT Filed: Jul. 8, 2003

(86) PCT No.: PCT/EP03/07321

§ 371 (c)(1),
(2), (4) Date: Jan. 3, 2005

(87) PCT Pub. No.: WO2004/004463

PCT Pub. Date: Jan. 15, 2004

(65) Prior Publication Data

US 2006/0166828 A1   Jul. 27, 2006

Related U.S. Application Data

(60) Provisional application No. 60/393,740, filed on Jul. 8, 2002.

(51) Int. Cl.
*A01N 43/90*  (2006.01)
*A01N 47/36*  (2006.01)
*A61K 31/00*  (2006.01)

(52) U.S. Cl. .................. 504/118; 504/129; 504/214

(58) Field of Classification Search .............. 504/116, 504/118, 129, 132, 135, 136, 139, 214
See application file for complete search history.

(56) References Cited

U.S. PATENT DOCUMENTS

| | | | |
|---|---|---|---|
| 5,846,907 A | 12/1998 | von Deyn et al. | |
| 6,124,469 A | 9/2000 | Rheinheimer et al. | |
| 6,486,096 B1 | 11/2002 | Hacker et al. | |
| 6,534,444 B1 | 3/2003 | Sievernich et al. | |
| 2002/0055435 A1 * | 5/2002 | Baltruschat et al. | 504/103 |

FOREIGN PATENT DOCUMENTS

| | | | |
|---|---|---|---|
| CA | 2334955 | * | 12/1999 |
| DE | 198 36 725 A1 | | 2/2000 |
| WO | WO 9741116 A1 | | 4/1996 |
| WO | WO 9741117 A1 | | 4/1996 |
| WO | WO 9741118 A1 | | 4/1996 |
| WO | WO 99/65314 A1 | | 12/1999 |
| WO | WO 02/087322 A2 | | 11/2002 |

* cited by examiner

Primary Examiner—Johann R Richter
Assistant Examiner—Andriae M Holt
(74) Attorney, Agent, or Firm—Rothwell, Figg, Ernst & Manbeck, P.C.

(57) ABSTRACT

A synergistic herbicidal mixture comprising
A) at least one 3-heterocyclyl-substituted benzoyl derivative of the formula I

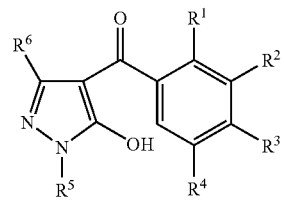

in which the variables have the following meanings:
$R^1$, $R^3$ are halogen, alkyl, haloalkyl, alkoxy, haloalkoxy, alkylthio, alkylsulfinyl or alkylsulfonyl;
$R^2$ is a optionally substituted heterocyclic radical selected from the group: isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl;
$R^4$ is hydrogen, halogen or alkyl;
$R^5$ is alkyl;
$R^6$ is hydrogen or alkyl;
or one of its environmentally compatible salts;
and
B) a synergistically effective amount of the compound of formula II

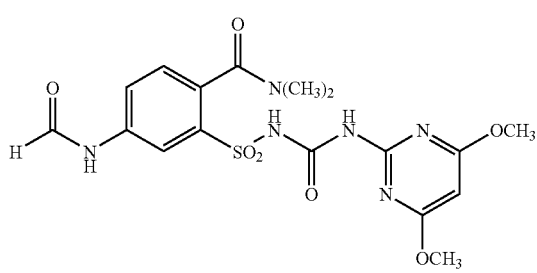

or one of its environmentally compatible salts;
and, if desired,
C) at least one further herbicidal compound;
and, if desired,
D) at least a safener.

Compositions comprising these mixtures, processes for the preparation of these compositions, and their use for controlling undesired plants.

20 Claims, No Drawings

SYNERGISTICALLY ACTING HERBICIDAL MIXTURES

CROSS REFERENCE TO RELATED APPLICATION

This application is a 35 USC §371 National Phase Entry Application from PCT/EP2003/007321, filed Jul. 8, 2003, and designating the U.S., which claims the priority of U.S. Provisional Application No. 60/393,740 filed Jul. 8, 2002.

The present invention relates to a synergistic herbicidal mixture comprising

A) at least one 3-heterocyclyl-substituted benzoyl derivative of the formula I

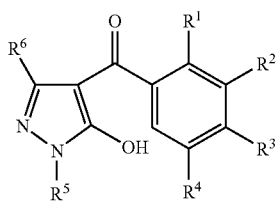

in which the variables have the following meanings:
$R^1$, $R^3$ are halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;
$R^2$ is a heterocyclic radical selected from the group: isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the six radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^4$ is hydrogen, halogen or $C_1$-$C_6$-alkyl;
$R^5$ is $C_1$-$C_6$-alkyl;
$R^6$ is hydrogen or $C_1$-$C_6$-alkyl;
or one of its environmentally compatible salts;

and
B) a synergistically effective amount of the compound of formula II

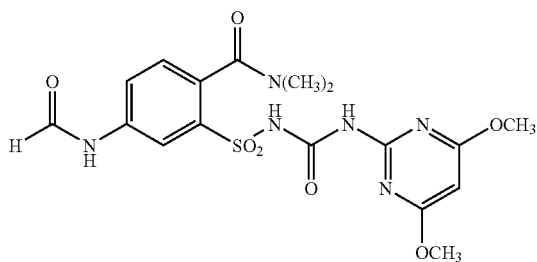

or one of its environmentally compatible salts;
and, if desired,
C) at least one herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS)—, glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides;

and, if desired,
D) a safening effective amount of at least one safener selected from the group of isoxadifen, mefenpyr and fenchlorazol;
or one of its environmentally compatible salts or esters.

The invention furthermore relates to herbicidal compositions comprising a herbicidally active amount of a synergistic herbicidal mixture as defined above and at least one liquid and/or solid carrier and, if desired, at least one surfactant.

Moreover, the invention relates to processes for the preparation of these compositions and to a method of controlling undesirable vegetation.

In crop protection products, it is always desirable to increase the specific activity of an active ingredient and the reliability of action. It is an object of the present invention to increase the activity and/or selectivity of the herbicidally active 3-heterocyclyl-substituted benzoyl derivatives of the formula I against undesirable harmful plants.

We have found that this object is achieved by the mixtures defined at the outset. We have furthermore found herbicidal compositions which comprise these mixtures, processes for their preparation, and methods of controlling undesirable vegetation. In the last-mentioned cases, it is irrelevant whether the herbicidally active compounds of the components A), B) and, if desired, C) and, if desired, D) are formulated and applied jointly or separately and in which sequence they are applied in the case of separate application.

The mixtures according to the invention show a synergistic effect; the compatibility of the herbicidally active compounds of components A), B) and, if desired, C) for certain crop plants is generally retained.

Suitable components C are, as acetyl-CoA carboxylase inhibitors (ACC), for example, cyclohexenone oxime ethers, phenoxyphenoxy-propionic esters or arylaminopropionic acids. The acetolactate synthase inhibitors (ALS) include, inter alia, imidazolinones, pyrimidyl ethers, sulfonamides or sulfonyl ureas. Relevant auxin herbicides are, inter alia, pyridine carboxylic-acids, 2,4-D or benazolin. Lipid biosynthesis inhibitors which are used are, inter alia, anilides, chloroacetanilides, thioureas, benfuresate or perfluidone. Suitable mitosis inhibitors are, inter alia, carbamates, dinitroanilines, pyridines, butamifos, chlorthal-dimethyl (DCPA) or maleic hydrazide. Examples of protoporphyrinogen IX oxidase inhibitors are, inter alia, diphenyl ethers, oxadiazoles, cyclic imides or pyrazoles. Suitable photosynthesis inhibitors are, inter alia, propanil, pyridate, pyridafol, benzothiadiazinones, dinitrophenols, dipyridylenes, ureas, phenols, chloridazon, triazine, triazinone, uracils or biscarbamates. The synergists are, inter alia, oxiranes. Examples of suitable growth substances are aryloxyalkanoic acids, benzoic acids or quinolinecarboxylic acids. The group "various other herbicide" is to be understood as meaning, inter alia, the classes of the active ingredients dicloropropionic acids, dihydrobenzofurans, phenylacetic acids and individual herbicides mentioned below whose mechanism of action is not (fully) understood.

Other suitable components C are active compounds selected from the group of the amides, auxin transport inhibitors, carotenoic biosynthesis inhibitors, enolpyruvylshikimate 3-phosphate synthase inhibitors (EPSPS), glutamine synthetase inhibitors and cell wall synthesis inhibitors.

Examples of herbicides which can be used in combination with the 3-heterocyclyl-substituted benzoyl derivatives of formula I and the compound of formula II according to the present invention are, inter alia:

C1 acetyl-CoA carboxylase inhibitors (ACC), for example
cyclohexenone oxime ethers, such as alloxydim, clethodim, cloproxydim, cycloxydim, sethoxydim, tralkoxydim, butroxydim, clefoxydim or tepraloxydim;
phenoxyphenoxypropionic esters, such as clodinafop-propargyl (and, if appropriate, cloquintocet), cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
arylaminopropionic acids, such as flamprop-methyl or flamprop-isopropyl;

C2 acetolactate synthase inhibitors (ALS), for example
imidazolinones, such as imazapyr, imazaquin, imazamethabenz-methyl (imazame), imazamoc, imazapic, imazethapyr or imazamethapyr;
pyrimidyl ethers, such as pyrithiobac-acid, pyrithiobac-sodium, bispyribac-sodium, K1H-6127 or pyribenzoxym;
sulfonamides, such as florasulam, flumetsulam or metosulam; or
sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]carbonyl]-2-(trifluoro-methyl)-benzenesulfonamide, sulfosulfuron or iodosulfuron;

C3 amides, for example
allidochlor (CDAA), benzoylprop-ethyl, bromobutide, chlorthiamid, diphenamid, etobenzanid (benzchlomet), fluthiamide, fosamin or monalide;

C4 auxin herbicides, for example
pyridinecarboxylic acids, such as clopyralid or picloram; or
2,4-D or benazolin;

C5 auxin transport inhibitors, for example
naptalame or diflufenzopyr;

C6 carotenoid biosynthesis inhibitors, for example
benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

C7 enolpyruvylshikimate-3-phosphate synthase inhibitors (EPSPS), for example
glyphosate or sulfosate;

C8 glutamine synthetase inhibitors, for example
bilanafos (bialaphos) or glufosinate-ammonium;

C9 lipid biosynthesis inhibitors, for example
anilides, such as anilofos or mefenacet;
chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;
thioureas, such as butylate, cycloate, di-allate, dimepiperate, EPTC, esprocarb, molinate, pebulate, prosulfocarb, thiobencarb (benthiocarb), tri-allate or vernolate; or
benfuresate or perfluidone;

C10 mitosis inhibitors, for example
carbamates, such as asulam, carbetamid, chlorpropham, orbencarb, pronamid (propyzamid), propham or tiocarbazil;
dinitroanilines, such as benefin, butralin, dinitramin, ethalfluralin, fluchloralin, oryzalin, pendimethalin, prodiamine or trifluralin;
pyridines, such as dithiopyr or thiazopyr; or
butamifos, chlorthal-dimethyl (DCPA) or maleic hydrazide;

C11 protoporphyrinogen IX oxidase inhibitors, for example
diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
oxadiazoles, such as oxadiargyl or oxadiazon;
cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
pyrazoles, such as ET-751, JV 485 or nipyraclofen;

C12 photosynthesis inhibitors, for example
propanil, pyridate or pyridafol;
benzothiadiazinones, such as bentazone;
dinitrophenols, for example bromofenoxim, dinoseb, dinoseb-acetate, dinoterb or DNOC;
dipyridylenes, such as cyperquat-chloride, difenzoquat-methylsulfate, diquat or paraquatt-dichloride;
ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
phenols, such as bromoxynil or ioxynil;
chloridazon;
triazines, such as ametryn, atrazine, cyanazine, desmetryn, dimethamethryn, hexazinone, prometon, prometryn, propazine, simazine, simetryn, terbumeton, terbutryn, terbutylazine or trietazine;
triazinones, such as metamitron or metribuzin;
uracils, such as bromacil, lenacil, or terbacil; or
biscarbamates, such as desmedipham or phenmedipham;

C13 synergists, for example
oxiranes, such as tridiphane;

C14 growth substances, for example
aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
benzoic acids, such as chloramben or dicamba; or
quinolinecarboxylic acids, such as quinclorac or quinmerac;

C15 cell wall synthesis inhibitors, for example
isoxaben or dichlobenil;

C16 various other herbicides, for example
dichloropropionic acids, such as dalapon;
dihydrobenzofurans, such as ethofumesate;
phenylacetic acids, such as chlorfenac (fenac); or aziprotryn, barban, bensulide, benzthiazuron, benzo-fluor, buminafos, buthidazole, buturon, cafenstrole, chlorbufam, chlorfenprop-methyl, chloroxuron, cin-methylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, suifallate (CDEC), terbucarb, triaziflam, triazofenamid or trimeturon;

or their environmentally compatible salts.

The 3-heterocyclyl-substituted benzoyl derivatives of the formula I are disclosed in WO 96/26206, WO 97/41116, WO 97/41117 and WO 97/41118, WO 98/31681.

The compound of formula II (common name foramsulfuron) is disclosed in U.S. Pat. No. 5,922,646.

The herbicidally active compounds from amongst groups C1 to C16 are described, for example, in "Herbizide [Herbicides]", Hock, Fedtke, Schmidt, 1st edition, Thieme 1995 (s. "quinclorac" p. 238, "molinat" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolynate" p. 146, "pyrazoxyfen" p. 146, "bensulfuronmethyl" p. 31, "pyrazosulfuron-ethyl" p. 31, "cinosulfuron" p. 31, "benfuresate" p. 233, "bromobutide" p. 243, "dymron" p. 243, "dimethyametryn" p. 118, "esprocarb" p. 229, "pyributicarb" p. 32, "cinemthylin" p. 32, "propanil" p. 32, "2,4-D" p. 30, "bentazon" p. 30, "azimsulfuron (DPX-A-8947)" p 175, "mecoprop-P" p. 237, "chlorpropham" p. 205, "ethoxyfen" p. 30, "haloxyfop-P-methyl" p. 38, "haloxyfop-ethoxyethyl" p. 38, "flumiclorac-pentyl" p. 35, "flupropacil" p. 143, "nipyraclofen" p. 145, "metosulam" p. 33, "ethametsulfuron-methyl" p. 36, "thifensulfuron-methyl" p. 35, "pyrithiobac acid" p. 181);

"Agricultural Chemicals", Book II Herbicides, 1993 (s. "thiobencarb" p. 85, "benzofenap" p. 221, "napropanilid" p. 49, "piperophos" p. 102, "anilofos" p. 241, "imazosulfuron (TH-913)" p. 150, "etobenzamid (HW-52)" p. 54, "sulcotrione (ICIA-0051)" p. 268, "poast" p. 253, "focus" p. 222, "dimethenamid" p. 48, "sulfosate" p. 236, "2,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazamethabenz-methyl" p. 153, "clodinafop-propargyl" p. 214, "fenoxaprop-P-ethyl" p. 208, "fluazifop-P-butyl" p. 207, "quizalofop-P-ethyl" p. 210, "quizalofop-terfuryl" p. 211, "flumioxazin" p. 43, "flumipropyn" p. 267, "sulfentrazone" p. 261, "thiazopyr" p. 226, "pyrithiobac-sodium" p. 266, "flumetsulam" p. 227, "amidosulfuron" p. 151, "halosulfuron-methyl" p. 148, "rimsulfuron" p. 138, "tribenuron-methyl" p. 139, "triflusulfuron-methyl" p. 137, "primisulfuron-methyl" p. 147);

"Agricultural Chemicals", Book II Herbicides, 13th Edition (s. "carfenstole" p. 284, "sulfosulfuron" p. 145, "ethoxy-sulfuron" p. 149, "pyribenzoxym" p. 279, "diflufenzopyr" p. 90, "ET-751" p. 278, "carfentrazone-ethyl" p. 267, "fluthiacet-methyl" p. 277, "imazapic" p. 160, "butenachlor" p. 54, "tiocarbazil" p. 84, "fluthiamide" p. 62, "isoxa-flutole" p. 283, "butroxydim" p. 259,);

"Short Review of Herbicides & PGRs 1991, Hodogaya Chemicals (s. "furyloxyfen" p. 142, "triazofenamid" p. 268, "thenylchlorid (NSK-850)" p. 52, "cumyluron (JC-940)" p. 90, "pendimethalin (AC-92553)" p. 58, "buthidazole" p. 88, "cyprazole" p. 38, "allidochlor" p. 48, "benzoylprop-ethyl" p. 38, "chlorthiamid" p. 150, "diphenamid" p. 34, "flamprop-methyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234, "glyphosate" p. 232, "amitrol" p. 254, "clomeprop p. 20, "dichlorprop" p. 6, "fenoprop" p. 8, "fluroxypyr" p. 156, "MCPA" p. 4, "MCPB" p. 8, "mecoprop" p. 6, "napropamide" p. 16, "triclopyr" p. 154, "chloramben" p. 28, "dicamba" p. 26, "clomazone" p. 268, "diflufenican" p. 42, "fluorochloridone" p. 266, "fluridone" p. 156, "asulam" p. 112, "barban" p. 100, "butylate" p. 106, "carbetamide" p. 36, "chlorobufam" p. 100, "cycloate" p. 108, "desmedipham" p. 104, "di-allate" p. 106, "EPTC" p. 108, "orbencarb" p. 112, "pebulate" p. 106, "phen-isopham" p. 118, "phenmedipham" p. 104, "propham" p. 100, "sulfallate" p. 110, "terbucarb" p. 102, "tri-allate" p. 108, "vernolate" p. 108, "acetochlor" p. 48, "alachlor" p. 46, "diethathyl-ethyl" p. 48, "dimethachlor" p. 50, "metolachlor" p. 46, "propachlor" p. 44, "pyrnachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54, "butralin" p. 58, "dinitramin" p. 56, "ethalfluralin" p. 60, "fluchloralin" p. 54, "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acifluorfen-sodium" p. 142, "aclonifen" p. 146, "bifenox" p. 140, "chlornitrofen" p. 138, "difenoxuron" p. 76, "fluorodifen" p. 138, "fluoroglycofen-ethyl" p. 146, "lactofen" p. 144, "nitrofen" p. 136, "nitrofluorfen" p. 140, "oxyfluorfen" p. 140, "cyperquat-chloride" p. 158, "difenzoquat-methylsulfate" p. 160, "diquat" p. 158, "paraquat-dichloride" p. 158, "benzthi-azuron" p. 82, "buturon" p. 66, "chlorbromuron" p. 72, "chloroxuron" p. 76, "chlorotoluron" p. 74, "cycluron" p. 84, "dimefuron" p. 88, "diuron" p. 70, "ethidimuron" p. 86, "fenuron" p. 64, "fluometuron" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "monuron" p. 64, "neburon" p. 72, "siduron" p. 68, "tebuthiuron" p. 86, "trimeturon" p. 64, "isocarbamid" p. 168, "imazamethapyr" p. 172, "imazapyr" p. 170, "imazaquin" p. 170, "imazethapyr" p. 172, "methazole" p. 162, "oxadiazon" p. 162, "tridiphane" p. 266, "bromoxynil" p. 148, nioxynil" p. 148, "diclofop-methyl" p. 16, "fenthiaprop-ethyl" p. 20, "fluazifop-butyl" p. 18, "haloxyfop-methyl" p. 18, "isoxapyrifop" p. 22, "propaquizafop" p. 24, "quizalo-fop-ethyl" p. 20, "chlorfenac" p. 258, "chlorfenprop-methyl" p. 258, "chloridazong p. 174, "maleic hydrazide" p. 162, "norflurazon" p.

174, "pyridate" p. 176, "clopyralid" p. 154, "picloram" p. 154, "chlorimuron-ethyl" p. 92, "chlorsulfuron" p. 92, "flazasulfuron" p. 96, "metsulfuron-methyl" S.92, "nicosulfuron" p. 96, "sulfometuron-methyl" p. 92, "tria-sulfuron" p. 94, "ametryn" p. 198, "atrazine" p. 188, "aziprotryne" p. 206, "cyanazine" p. 192, "cyprazine" p. 192, "desmetryne" p. 200, "dipropetryn" p. 202, "eglinazine-ethyl" p. 208, "hexazinone" p. 208, "procyazine" p. 192, "prometone" p. 196, "prometryn" p. 196, "propazine" p. 188, "secbumeton" p. 196, "simazine" p. 188, "simetryn" p. 196, "terbumeton" p. 204, "terbutryn" p. 198, "terbutylazine" p. 190, "trietazine" p. 188, "ethiozine" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos." p. 228, "DCPA" p. 28, "dichlobenil" p. 148, "endothal" p. 264, "mefluidide" p. 306, "perfluidone" p. 260, "terbuchlor" p. 48);

"Global Herbicide Directory" First Edition, 1994 (s. "oxadi-argyl" p. 96);

"European Directory of Agrochemical Products" Volume 2-Herbicides" Fourth Edition, (s. "buminafos" p. 255).

Moreover, the compound "DEH-112" is disclosed in European Patent Application EP-A 302 203. The compound "tepraloxydim" is described in DE-A 33 36 140; the compound "cinidon-ethyl" in DE-A 36 03 789 and the compound "fluorbentranil" in EP-A 84 893. Other compounds are known from "Brighton Crop Protection Conference—Weeds—1993" (S. "thidiazimin" p. 29, "AC-322140" p. 41, "KIE-6127" p. 47, "prosulfuron" p. 53, "K1H-2023" p. 61, "metobenzuron" p. 67). The compound "carfenstrole (CH-900)" is mentioned in EP-A 332 133, and the compound N-[[[4-methoxy-6-(trifluoro-methyl)-1,3,5-triazin-2-yl] amino]-carbonyl]-2-(trifluoromethyl-benzenesulfonamide) is described in PCT/EP 96/03996.

The assignment of the active ingredients to the respective mechanisms of action is based on current knowledge. If several mechanisms of action apply to one active ingredient, this substance was only assigned to one mode of action.

The above mentioned safeners (component D) are described, for example, in "Herbizide [Herbicides]" Hock, Fedtke, Schmidt, 1st edition, Thieme 1995 ("fenchlorazol" p. 266), WO 91/07874 ("mefenpyr") and WO 95/07897 ("isoxadifen").

The 3-heterocyclyl-substituted benzoyl derivatives of the formula I can exist, or be used, in the form of the pure enantiomers and also as racemates or diastereomer mixtures.

The 3-heterocyclyl-substituted benzoyl derivatives of the formula I and/or the compound of formula II and/or the herbicidally active compounds from amoungs groups C1 to C16 and/or the safeners may also exist in the form of their environmentally compatible salts. Suitable salts are, in general, the salts of those cations, or the acid addition salts of those acids, whose cations, or anions, respectively, do not adversely affect the herbicidal action of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$-$C_4$-alkyl, hydroxy-$C_1$-$C_4$-alkyl, $C_1$-$C_4$-alkoxy-$C_3$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl ammonium, di(2-hydroxyeth-1-yl)ammonium, trimethylbenzylammonium, furthermore phosphonium ions, sulfonium ions, preferably tri($C_1$-$C_4$-alkyl)sulfonium and sulfoxonium ions, preferably, tri($C_1$-$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$-$C_4$-alkanoic acids, preferably formate, acetate, propionate and butyrate.

The safeners may also exist in form of their environmentally compatible esters. Suitable esters are alkyl-, alkoxyalkyl-, allyl-, propargyl- and oxetan-3-ylesters, preferably $C_1$-$C_{10}$ alkylesters, for example methyl-, ethyl-, propyl-, isopropyl-, butyl-, isobutyl-, pentyl-, mexyl-(1-ethyl-hexyl-) or isooctyl-(2-ethylhexyl-)esters, $C_1$-$C_4$-alkoxyethylesters, for example methoxyethyl-, ethoxyethyl- or butoxyethylesters, allylesters, propargylesters and oxetan-3-ylesters.

As a rule the ethyl esters of isoxadifen, mefenpyr and fenchlorazol are preferred.

Preferred with regard to the synergistic herbicidal action of the mixtures according to the invention are those 3-heterocyclyl-substituted benzoyl derivatives of the formula I in which the variables have the following meanings, either alone or in combination:

$R^1$ halogen such as chlorine or bromine, $C_1$-$C_6$-alkyl such as methyl or ethyl or $C_1$-$C_6$-alkylsulfonyl such as methylsulfonyl or ethylsulfonyl; especially preferably chlorine, methyl or methylsulfonyl;

$R^2$ a heterocyclic radical selected from the group: isoxazol-3-yl, isoxazol-5-yl and 4,5-dihydroisoxazol-3-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio; especially preferably isoxazol-5-yl, 3-methyl-isoxazol-5-yl, 4,5-dihydroisoxazol-3-yl, 5-methyl-4,5-dihydroisoxazol-yl, 5-S ethyl-4,5-dihydroisoxazol-3-yl or 4,5-dimethyl-4,5-dihydroisoxazol-3-yl;

$R^3$ halogen such as chlorine or bromine or $C_1$-$C_6$-alkylsulfonyl such as methylsulfonyl or ethylsulfonyl; especially preferably chlorine, methylsulfonyl or ethylsulfonyl; $R^4$ hydrogen or methyl; especially preferably hydrogen;

$R^5$ is $C_1$-$C_6$-alkyl, such as methyl, ethyl, propyl, 1-methylethyl, butyl, 1-methylpropyl or 2-methylpropyl; especially preferably methyl, ethyl or 1-methylethyl;

$R^6$ hydrogen or $C_1$-$C_6$-alkyl, such as methyl or ethyl; especially preferably hydrogen or methyl.

Very particularly preferred are those 3-heterocyclyl-substituted benzoyl derivatives of the formula Ia, in particular the compounds Ia.1 to Ia.47, which are mentioned in Table 1 which

TABLE 1

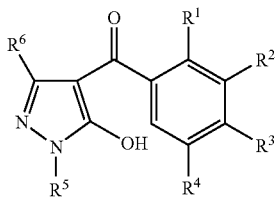

I

| No. | R¹ | R² | R³ | R⁴ | R⁵ | R⁶ |
|---|---|---|---|---|---|---|
| Ia.1 | Cl | 4,5-dihydroisoxazol-3-yl | SO₂CH₃ | H | CH₃ | CH₃ |
| Ia.2 | Cl | 4,5-dihydroisoxazol-3-yl | Cl | H | CH₃ | CH₃ |
| Ia.3 | Cl | 4,5-dihydroisoxazol-3-yl | SO₂CH₃ | H | CH₃ | H |
| Ia.4 | Cl | 4,5-dihydro-5-methylisoxazol-3-yl | SO₂CH₃ | H | CH₃ | H |
| Ia.5 | Cl | 4,5-dihydro-5,5-dimethylisoxazol-3-yl | SO₂CH₃ | H | CH₃ | H |
| Ia.6 | Cl | 4,5-dihydro-5-ethylisoxazol-3-yl | SO₂CH₃ | H | CH₃ | H |
| Ia.7 | Cl | 4,5-dihydro-5,5-diethylisoxazol-3-yl | SO₂CH₃ | H | CH₃ | H |
| Ia.8 | Cl | 4,5-dihydro-5-chloromethylisoxazol-3-yl | SO₂CH₃ | H | CH₃ | H |
| Ia.9 | Cl | 4,5-dihydro-5-ethoxyisoxazol-3-yl | SO₂CH₃ | H | CH₃ | H |
| Ia.10 | Cl | 4,5-dihydro-5-methoxyisoxazol-3-yl | SO₂CH₃ | H | CH₃ | H |
| Ia.11 | Cl | 4,5-dihydro-4,5-dimethylisoxazol-3-yl | SO₂CH₃ | H | CH₃ | H |
| Ia.12 | Cl | 4,5-dihydro-5-thioethylisoxazol-3-yl | SO₂CH₃ | H | CH₃ | H |
| Ia.13 | Cl | 4,5-dihydro-5-trifluoromethylisoxazol-3-yl | SO₂CH₃ | H | CH₃ | H |
| Ia.14 | Cl | 4,5-dihydroisoxazol-3-yl | SO₂CH₃ | H | C₂H₅ | H |
| Ia.15 | Cl | 4,5-dihydroisoxazol-3-yl | Cl | H | C₂H₅ | H |
| Ia.16 | Cl | 4,5-dihydro-5-methylisoxazol-3-yl | SO₂CH₃ | H | C₂H₅ | H |
| Ia.17 | Cl | 4,5-dihydro-5,5-dimethylisoxazol-3-yl | SO₂CH₃ | H | C₂H₅ | H |
| Ia.18 | Cl | 4,5-dihydro-5-ethylisoxazol-3-yl | SO₂CH₃ | H | C₂H₅ | H |
| Ia.19 | Cl | 4,5-dihydro-5,5-diethylisoxazol-3-yl | SO₂CH₃ | H | C₂H₅ | H |
| Ia.20 | Cl | 4,5-dihydro-5-chloromethylisoxazol-3-yl | SO₂CH₃ | H | C₂H₅ | H |
| Ia.21 | Cl | 4,5-dihydroisoxazol-3-yl | SOCH₃ | H | C₂H₅ | H |
| Ia.22 | Cl | 4,5-dihydro-5-ethoxyisoxazol-3-yl | SO₂CH₃ | H | C₂H₅ | H |
| Ia.23 | Cl | 4,5-dihydro-4,5-dimethylisoxazol-3-yl | SO₂CH₃ | H | C₂H₅ | H |
| Ia.24 | Cl | 4,5-dihydro-5-thioethylisoxazol-3-yl | SO₂CH₃ | H | C₂H₅ | H |
| Ia.25 | Cl | 4,5-dihydro-5-trifluoromethylisoxazol-3-yl | SO₂CH₃ | H | C₂H₅ | H |
| Ia.26 | Cl | 4,5-dihydroisoxazol-3-yl | SO₂CH₃ | H | i-C₄H₉ | H |
| Ia.27 | CH₃ | 4,5-dihydroisoxazol-3-yl | SO₂CH₃ | H | CH₃ | CH₃ |
| Ia.28 | CH₃ | 4,5-dihydroisoxazol-3-yl | Cl | H | CH₃ | CH₃ |
| Ia.29 | CH₃ | 4,5-dihydroisoxazol-3-yl | SO₂CH₃ | H | CH₃ | H |
| Ia.30 | CH₃ | 4,5-dihydro-5-methylisoxazol-3-yl | SO₂CH₃ | H | CH₃ | H |
| Ia.31 | CH₃ | 4,5-dihydro-5,5-dimethylisoxazol-3-yl | SO₂CH₃ | H | CH₃ | H |
| Ia.32 | CH₃ | 4,5-dihydro-5-ethylisoxazol-3-yl | SO₂CH₃ | H | CH₃ | H |
| Ia.33 | CH₃ | 4,5-dihydro-5,5-diethylisoxazol-3-yl | SO₂CH₃ | H | CH₃ | H |
| Ia.34 | CH₃ | 4,5-dihydroisoxazol-3-yl | SO₂CH₃ | H | CH₃ | H |
| Ia.35 | CH₃ | 4,5-dihydro-4,5-dimethylisoxazol-3-yl | SO₂CH₃ | H | CH₃ | H |
| Ia.36 | CH₃ | 4,5-dihydroisoxazol-3-yl | SO₂CH₃ | H | C₂H₅ | H |
| Ia.37 | CH₃ | 4,5-dihydroisoxazol-3-yl | Cl | H | C₂H₅ | H |
| Ia.38 | CH₃ | 4,5-dihydro-5-methylisoxazol-3-yl | SO₂CH₃ | H | C₂H₅ | H |
| Ia.39 | CH₃ | 4,5-dihydro-5,5-dimethylisoxazol-3-yl | SO₂CH₃ | H | C₂H₅ | H |
| Ia.40 | CH₃ | 4,5-dihydro-5-ethylisoxazol-3-yl | SO₂CH₃ | H | C₂H₅ | H |
| Ia.41 | CH₃ | 4,5-dihydro-5,5-diethylisoxazol-3-yl | SO₂CH₃ | H | C₂H₅ | H |
| Ia.42 | CH₃ | 4,5-dihydro-4,5-dimethylisoxazol-3-yl | SO₂CH₃ | H | C₂H₅ | H |
| Ia.43 | CH₃ | 4,5-dihydroisoxazol-3-yl | SO₂CH₃ | H | i-C₄H₉ | H |
| Ia.44 | Cl | 3-methylisoxazol-5-yl | SO₂CH₃ | H | CH₃ | H |
| Ia.45 | Cl | 3-methylisoxazol-5-yl | SO₂CH₃ | H | C₂H₅ | H |
| Ia.46 | CH₃ | 3-methylisoxazol-5-yl | SO₂CH₃ | H | CH₃ | H |
| Ia.47 | CH₃ | 3-methylisoxazol-5-yl | SO₂CH₃ | H | C₂H₅ | H |

Also very particularly preferred are the compounds Ib, in particular the compounds Ib.1 to Ib.47, which differ from the compounds Ia.1 to Ia.47 only by the fact that they are present as the sodium salt:

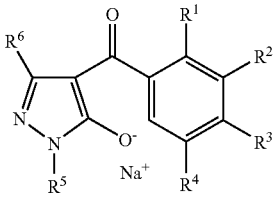

Ib

Also very particularly preferred are the compounds Ic, in particular the compounds Ic.1 to Ic.47, which differ from the compounds Ia.1 to Ia.47 only by the fact that they are present as the lithium salt:

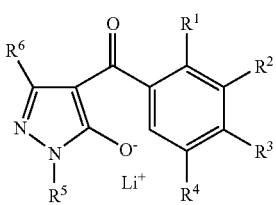

Ic

Also very particularly preferred are the compounds Id, in particular the compounds Id.1 to Id.47, which differ from the compounds Ia.1 to Ia.47 only by the fact that they are present as the potassium salt:

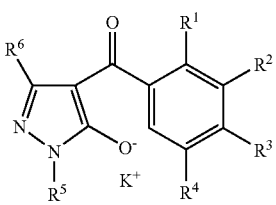

Id

Also very particularly preferred are the compounds Ie, in particular the compounds Ie.1 to Ie.47, which differ from the compounds Ia.1 to Ia.47 only by the fact that they are present as the ammonium salt:

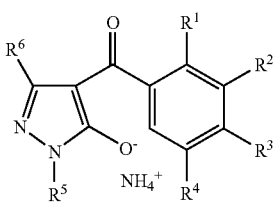

Ie

Very particularly preferred are, especially, the compounds Ia, especially the compounds Ia.1 to Ia.47.

Very particularly preferred are, moreover, the 3-heterocyclyl-substituted benzoyl derivatives of the formula I, where
$R^4$ is hydrogen.

Very particularly preferred are, moreover, the 3-heterocyclyl substituted benzoyl derivatives of the formula I where
$R^2$ is a heterocyclic radical selected from the group: isoxazol-3-yl, isoxazol-4-yl and isoxazol-5-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio.

Very particularly preferred are, especially, the 3-heterocyclyl-substituted benzoyl derivatives of the formula I, where
$R^2$ is isoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^4$ is hydrogen.

Very particularly preferred are also, especially, the 3-heterocyclyl-substituted benzoyl derivatives of the formula I where
$R^2$ is isoxazol-5-yl, which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^4$ is hydrogen.

Most particularly preferred is 4-[2-chloro-3-(3-methyl-isoxazol-5-yl)-4-methylsulfonyl-benzoyl]-1-methyl-5-hydroxy-1H-pyrazole.

Most particularly preferred is also 4-[2-methyl-3-(3-methyl-isoxazol-5-yl)-4-methylsulfonyl-benzoyl]-1-methyl-5-hydroxy-1H-pyrazole.

Very particularly preferred are, moreover, the 3-heterocyclyl-substituted benzoyl derivatives of the formula I where
$R^2$ is a heterocyclic radical selected from the group: 4,5-dihydroisoxazol-3-yl, 4,5-dihydroisoxazol-4-yl and 4,5-dihydroisoxazol-5-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio.

Very particularly preferred are, especially, the 3-heterocyclyl-substituted benzoyl derivatives of the formula I where
$R^2$ is 4,5-dihydroisoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^4$ is hydrogen.

Most particularly preferred are the 3-heterocyclyl-substituted benzoyl derivatives of the formula I where
$R^1$ is halogen or $C_1$-$C_6$-alkyl; and
$R^2$ is 4,5-dihydroisoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^3$ is $C_1$-$C_6$-alkylsulfonyl;
$R^4$ is hydrogen.

Most especially preferred is −4-[2-chloro-3-(4,5-dihydroisoxazol-3-yl)-4-methylsulfonylbenzoyl]-1-methyl-5-hydroxy-1H-pyrazole.

Most particularly preferred is also 4-[2-methyl-3-(4,5-dihydroisoxazol-3-yl)-4-methylsulfonyl-benzoyl]-1-methyl-5-hydroxy-1H-pyrazole.

In a further particular embodiment, the synergistic herbicidal mixture comprises, two herbicidal active compounds, a compound of formula I (component A) and the compound of formula II (component B).

For particular preferred embodiments, the respective preferences described above apply analogously.

In particular the synergistic herbicidal mixture comprises as component A 4-[2-methyl-3-(4,5-dihydroisoxazol-3-yl)-4-methylsulfonyl-benzoyl]-1-methyl-5-hydroxy-1H-pyrazole and as component B the compound of formula II.

In a further particular embodiment, the synergistic herbicidal mixture comprises, at least three herbicidal active compounds, a compound of formula I (component A), the compound of formula II (component B) and C) at least one herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

For particular preferred embodiments, the respective preferences described above apply analogously.

With a view to the synergistic herbicidal action of the mixtures comprising a component A), B) and C) according to the invention, compounds from amongst groups C1 to C14 or C16, preferably from amongst groups C2, C6 and C12, especially from amongst groups C6 and C12, are preferred as component C).

In particular, compounds from amongst the classes of active ingredients mentioned below are preferred, or the following compounds are very particularly preferred:

C1 acetyl-CoA carboxylase inhibitors (ACC)

cyclohexenone oxime ethers, in particular cycloxydim, sethoxydim or tralkoxydim, preferably sethoxydim or tralkoxydim; or phenoxyphenoxypropionic esters, in particular clodinafop-propargyl (and, if appropriate, cloquintocet), fenoxaprop-ethyl or fenoxaprop-P-ethyl, preferably clodinafop-propargyl (and, if appropriate, cloquintocet) or fenoxaprop-P-ethyl;

C2 acetolactate synthase inhibitors (ALS):

imidazolinones, in particular imazapyr, imazaquin, imazamethabenz, imazethapyr or imazamoc, preferably imazapyr;

pyrimidyl ethers, in particular pyrithiobac sodium;

sulfonamides, in particular florasulam, flumetsulam or metosulam, preferably metosulam; or sulfonylureas, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron; especially halosulfuron-methyl, nicosulfuron, primisulfuron-methyl, prosulfuron, rimsulfuron, thifensulfuron-methyl tribenuron-methyl, N-[[[4-methoxy-6-(trifluoromethyl)-1,3,5-triazin-2-yl]-amino]-carbonyl]-2-(trifluoromethyl)-benzenesulfonamide or sulfosulfuron;

C3 amides:

fluthiamide;

C4 auxin herbicides:

pyridinecarboxylic acids, in particular clopyralid; or 2,4-D;

C5 auxin transport inhibitors:

diflufenzopyr;

C6 carotenoid biosynthesis inhibitors:

isoxaflutole, mesotrione, isoxachloride, ketospiradox or sulcotrione (chlormesulone), in particular isoxaflutole or sulcotrione;

C7 enolpyruvylshikimate-3-phosphate synthase inhibitors (EPSPS):

glyphosate or sulfosate;

C8 glutamin synthetase inhibitors:

glufosinate-ammonium;

C9 lipid biosynthesis inhibitors:

chloroacetanilides, in particular dimethenamid, S-dimethenamid, acetochlor, metolachlor or S-metolachlor, thioureas, in particular benthiocarb;

C10 mitosis inihibitors:

dinitroanilines, in particular pendimethalin;

C11 protoporphyrinogen IX oxidase inhibitors:

diphenyl ethers, in particular acifluorfen or acifluorfen-sodium;

oxadiazoles, in particular oxadiargyl; or cyclic imides, in particular butafenacil, carfentrazone-ethyl, cinidon-ethyl or flumiclorac-pentyl, preferably carfentrazone-ethyl, cinidon-ethyl or flumidorac-pentyl;

pyrazoles, in particular JV 85;

C12 photosynthesis inhibitors:

pyridate or pyridafol, in particular pyridate;

benzothiadiazinones, in particular bentazone;

dipyridylenes, in particular paraquat-dichloride;

ureas, in particular diuron or isoproturon, preferably diuron;

phenols, in particular bromoxynil;

chloridazone;

triazines, in particular atrazine or terbutylazine; or triazinones, in particular metribuzin;

C13 synergists:

oxiranes, in particular tridiphane;

C14 growth substances:

aryloxyalkanoic acids, in particular fluoroxypyr, MCPA or mecoprop-P;

benzoic acids, in particular dicamba; or quinolinecarboxylic acids, in particular quinclorac;

C16 various other herbicides:

triaziflam.

In particular, compounds from amongst the classes of active ingredients mentioned below are preferred, or the following—compounds are very particularly preferred.

C2 acetolactate synthase inhibitors (ALS):

imidazolinones, in particular imazapyr, imazaquin, imazamethabenz, imazethapyr or imazamoc, preferably imazapyr;

pyrimidyl ethers, in particular pyrithiobac sodium;

sulfonamides, in particular florasulam, flumetsulam or metosulam, preferably metosulam; or sulfonylureas, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron; especially halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfon-amide or sulfo-sulfuron;

C6 carotenoid biosynthesis inhibitors:

isoxaflutole or sulcotrione, preferably isoxaflutole;

C12 photosynthesis inhibitors:

pyridate;

benzothiadiazinones, in particular bentazone;

dipyridylenes, in particular paraquat-dichloride;

ureas, in particular diuron or isoproturon, preferably diuron;
phenols, in particular bromoxynil;
chloridazon;
triazines, in particular atrazine or terbutylazine; or
triazinones, in particular metribuzin;

Preferably compounds from amongst the classes C6 and C12 as mentioned above are preferred.

Especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a sulfonylurea, in particular iodosulfuron.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C isoxaflutole.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C pyridate.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a benzothiadiazinones, in particular bentazone.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a triazine, in particular atrazine.

In a further particular embodiment, the synergistic herbicidal mixture comprises, at least two herbicidal active compounds, a compound of formula I (component A), the compound of formula II (component B) and D) a safening effective amount of at least one safener selected from the group of isoxadifen, mefenpyr and fenchlorazol.

Especially preferred are synergistic herbicidal mixtures which comprise as component A 4-[2-methyl-3-(4,5-dihydroisoxazol-3-yl)-4-methylsulfonyl-benzoyl]-1-methyl-s-hydroxy-1H-pyrazole, as component B the compound of formula II and as component D isoxadifen.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component D mefenpyr.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component D fenchlorazol.

In a further particular embodiment, the synergistic herbicidal mixture comprises, at least three herbicidal active compounds, a compound of formula I (component A), the compound of formula II (component B) and C) at least one herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (BPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides; and D) a safening effective amount of at least one safener selected from the group of isoxadifen, mefenpyr and fenchlorazol.

With a view to the synergistic herbicidal action of the mixtures comprising a component A), B), C) and D) according to the invention, compounds from amongst groups C1 to C14 or C16, preferably from amongst groups C2, C6 and C12, especially from amongst groups C6 and C12, are preferred as component C).

In particular those of the above mentioned mixtures are preferred wherein the safener is isoxadifen.

Also those of the above mentioned mixtures are preferred wherein the safener is mefenpyr.

Also those of the above mentioned mixtures are preferred wherein the safener is fenchlorazol.

Especially those of the above mentioned mixtures are preferred wherein the component C) is selected from amongst the classes of active ingredients mentioned below, or the following compounds:

C2 acetolactate synthase inhibitors (ALS)
imidazolinones, in particular imazapyr, imazaquin, imazamethabenz, imazethapyr or imazamoc, preferably imazapyr;
pyrimidyl ethers, in particular pyrithiobac sodium;
sulfonamides, in particular florasulam, flumetsulam or metosulam, preferably metosulam; or
sulfonylureas, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron;

C6 carotenoid biosynthesis inhibitors:
isoxaflutole or sulcotrione, preferably isoxaflutole;

C12 photosynthesis inhibitors:
pyridate;
benzothiadiazinones, in particular bentazone;
dipyridylenes, in particular paraquat-dichloride;
ureas, in particular diuron or isoproturon, preferably diuron;
phenols, in particular bromoxynil;
chloridazon;
triazines, in particular atrazine or terbutylazine; or
triazinones, in particular metribuzin.

Extraordinary preferred are synergistic herbicidal mixtures which comprise as component A 4-[2-methyl-3-(4,5-dihydroisoxa-zol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]-carbonyl]-2-(trifluoromethyl)-benzenesulfonamide, iodo-sulfuron or sulfosulfuron, and as component D isoxadifen.

In particular extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C iodosulfuron and as component D isoxadifen.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and as component D mefenpyr.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and as component D fenchlorazol.

In a further particular embodiment, the synergistic herbicidal mixture comprises, at least four herbicidal active compounds, a compound of formula I (component A), the compound of formula II (component B) and C) at least two herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides; and D) a safening effective amount of at least one safener selected from the group of isoxadifen, mefenpyr and fenchlorazol.

With a view to the synergistic herbicidal action of the mixtures comprising a component A), B), C) and D) according to the invention, compounds from amongst groups C1 to C14 or C16, preferably from amongst groups C2, C6 and C12, especially from amongst groups C6 and C12 are preferred as component C).

In particular those of the above mentioned mixtures are preferred wherein the safener is isoxadifen.

Also those of the above mentioned mixtures are preferred wherein the safener is mefenpyr.

Also those of the above mentioned mixtures are preferred wherein the safener is fenchlorazol.

Especially those of the above mentioned mixtures are preferred wherein the two herbicides of the component C) are selected from amongst the classes of active ingredients mentioned below, or the following compounds:

C2 acetolactate synthase inihibitors (ALS):
  imidazolinones, in particular imazapyr, imazaquin, imazamethabenz, imazethapyr or imazamoc, preferably imazapyr;
  pyrimidyl ethers, in particular pyrithiobac sodium;
  sulfonamides, in particular florasulam, flumetsulam or metosulam, preferably metosulam; or
  sulfonylureas, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron;

C6 carotenoid biosynthesis inhibitors:
  isoxaflutole or sulcotrione, preferably isoxaflutole;

C12 photosynthesis inhibitors:
  pyridate;
  benzothiadiazinones, in particular bentazone;
  dipyridylenes, in particular paraquat-dichloride;
  ureas, in particular diuron or isoproturon, preferably diuron;
  phenols, in particular-bromoxynil;
  chloridazon;
  triazines, in particular atrazine or terbutylazine; or
  triazinones, in particular metribuzin.

Extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]amino]carbonyl]-2-(trifluoromethyl)-benzenesulfonamide, iodosulfuron or sulfosulfuron, and a triazine, in particular atrazine or terbutylazine, and as component D isoxadifen.

In particular extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C iodosulfuron and atrazine, and as component D isoxadifen.

Also in particular extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C iodosulfuron and pyridate, and as component D isoxadifen.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and a benzothiadiazinone, in particular bentazone, and as component D isoxadifen.

In particular extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C iodosulfuron and bentazone, and as component D isoxadifen.

Extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and a triazine, in particular atrazine or terbutylazine, and as component D mefenpyr.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and pyridate, and as component D mefenpyr.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and a benzothiadiazinone, in particular bentazone, and as component D mefenpyr.

Extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and a triazine, in particular atrazine or terbutylazine, and as component D fenchlorazol.

Also extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron, thifensulfuron-methyl, tribenuron-methyl, is N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and pyridate, and as component D fenchlorazol.

Also extraordinary preferred are synergistic herbicidal mixtures which comprise as component A 4-[2-methyl-3-(4,5-dihydrois-oxazol-3-yl)-4-methylsulfonyl-benzoyl]-1-methyl-5-hydroxy-1H-pyrazole, as component B the compound of formula II, as component C a sulfonylurea, in particular halosulfuron-methyl, nicosulfuron, primisulfuron-methyl, prosulfuron, rimsulfuron; thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide, iodosulfuron or sulfosulfuron, and a benzothiadiazinone, in particular bentazone, and as component D fenchlorazol.

The present invention also extends to herbicidal compositions which comprise a herbicidally active amount of a synergistic herbicidal mixture (comprising components A), B) and, if desired, C) and, if desired, D) as described above), at least one liquid and/or solid carrier and, if desired, at least one surfactant.

The herbicidal compositions and synergistic herbicidal mixtures according to the invention can effect very good control of broad-leaved weeds and grass weeds in crops such as maize, cereals, rice and soya without damaging the crop plants, an effect observed especially even at low rates of application.

Taking into consideration the variety of application method in question, the herbicidal compositions and synergistic herbicidal mixtures according to the invention can additionally be employed in a further number of crop plants for eliminating undesirable plants. Examples of suitable crops are the following: *Allium cepa, Ananas comosus, Arachis hypogaea, Asparagus officinalis, Beta vulgaris* ssp. altissima, *Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* und *Zea mays.*

Moreover, the herbicidal compositions and synergistic herbicidal mixtures according to the invention can also be used in crops which tolerate the action of herbicides due to breeding, including genetic engineering methods.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The components A) and B) and, if desired, C) and, if desired, D) can be formulated jointly, but also separately, and/or applied to the plants, their environment and/or seeds jointly or separately. It is preferable to apply the active ingredients simultaneously. However, it is also possible to apply them separately.

Moreover, it may be advantageous to apply the herbicidal compositions and synergistic herbicidal mixtures according to the invention, jointly or separately, with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The mixtures according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise components A), B) and, if desired, C) and, if desired, D) in such weight ratios that the synergistic effect takes place.

The ratios of component A) and B) in the mixture preferably range from 1:0.001 to 1:500, preferably from 1:0.01 to 1:100, particularly preferably from 1:0.1 to 1:50.

The ratios of components A) and C) in the mixture preferably range from 1:0.002 to 1:800, preferably from 1:0.003 to 1:250, particularly preferably from 1:0.003 to 1:160, especially preferably from 1:0.02 to 1:250, extraordinary preferably from 1:0.02 to 1:160.

The ratios of components A) and D) in the mixture preferably range from 1:0.002 to 1:800, preferably from 1:0.003 to 1:250, particularly preferably from 1:0.02 to 1:160.

The rate of application of pure synergistic herbicidal mixture, i.e. without formulation auxiliaries, amounts to 0.2 to 5000 g/ha, preferably 2 to 2000 g/ha, in particular 8 to 1000 g/ha, of active substance (a.s.), depending on the intended aim, the season, the target plants and growth stage.

The rate of application of 3-heterocyclyl-substituted benzoyl derivative of the formula I is 0.1 to 250 g/ha, as a rule 5 to 250 g/ha, preferably 10 to 150 g/ha, of active substance (a.s.).

The preferred rate of application of the compound of formula II is 0.1 to 250 g/ha, as a rule 1 to 120 g/ha, preferably 10 to 100 g/ha, of active substance (a.s.)

The preferred application rate of the active ingredients of the optional component C are compiled in Table 2.

TABLE 2

| Component C | | Class of active ingredient | Active ingredient | Rate of application (g/ha) |
|---|---|---|---|---|
| C1 | acetyl-CoA carboxylase inhibitors | | | 25-400 |
| | | cyclohexenone oxime ethers | | 100-400 |
| | | | cycloxydim | 100-400 |
| | | | sethoxydim | 100-400 |
| | | | tralkoxydim | 100-400 |
| | | phenoxyphenoxypropionic esters | | 25-300 |
| | | | clodinafpop-P-propargyl[a] | 25-100 |
| | | | fenoxaprop-ethyl | 50-300 |
| | | | fenoxaprop-P-ethyl | 25-150 |
| C2 | acetolactate synthase inhibitors (ALS) | | | 0.1-800 |
| | | imidazolinones | | 20-800 |
| | | | imazapyr | 30-400 |
| | | | imazaquin | 50-300 |
| | | | imazamethabenz | 100-800 |
| | | | imazethapyr | 30-150 |
| | | | Imazamox | 20-120 |
| | | pyrimidyl ethers | | 2-120 |
| | | | pyrithiobac-sodium | 2-120 |
| | | sulfonamides | | 1-225 |
| | | | florasulam | 1-20 |
| | | | flumetsulam | 25-225 |
| | | | metosulam | 1-60 |
| | | sulfonylureas | | 0.1-120 |

TABLE 2-continued

| Component C | | Class of active ingredient | Active ingredient | Rate of application (g/ha) |
|---|---|---|---|---|
| | | | halosulfuron-methyl | 5-120 |
| | | | nicosulfuron | 1-120 |
| | | | primisulfuron-methyl | 10-120 |
| | | | prosulfuron | 10-120 |
| | | | rimsulfuron | 5-120 |
| | | | thifensulfuron-methyl | 10-60 |
| | | | tribenuron-methyl | 10-60 |
| | | | N-[[[4-methoxy-6-(trifluoromethyl)-1,3,5-triazin-2-yl]amino]carbonyl]-2-(trifluoromethyl)benzenesulfonamide | 5-120 |
| | | | iodosulfuron | 0.1-10 |
| | | | sulfosulfuron | 10-60 |
| C3 | amides | | | 250-2000 |
| | | — | fluthiamide | 250-2000 |
| C4 | auxin herbicides | | | 25-750 |
| | | pyridinecarboxylic acids | | 25-750 |
| | | | clopyralid | 25-750 |
| | | — | 2,4-D | 50-750 |
| C5 | auxin transport inhibitors | | | 15-100 |
| | | — | diflufenzopyr | 15-100 |
| C6 | carotenoid biosynthesis inhibitors | | | 25-600 |
| | | — | isoxaflutole | 25-200 |
| | | — | sulcotrione | 100-600 |
| | | — | mesotrione | 25-300 |
| | | — | isoxachlortole | 25-200 |
| | | — | ketospiradox | 25-300 |
| C7 | enolpyruvylshikimat-3-phosphate synthase inhibitors (EPSPS) | | | 360-1080 |
| | | — | glyphosate | 360-1080 |
| | | — | sulfosate | 360-1080 |
| C8 | glutamine synthetase inhibitors | | | 10-600 |
| | | — | glufosinate-ammonium | 10-600 |
| C9 | lipid biosynthesis inhibitors | | | 60-4000 |
| | | chloroacetanilides | | 60-4000 |
| | | | dimethenamid | 60-2000 |
| | | | S-dimethenamid | 60-2000 |
| | | | acetochlor | 250-4000 |
| | | | metolachlor | 60-4000 |
| | | | S-metolachlor | 60-4000 |
| | | thioureas | | 100-4000 |
| | | | benthiocarb | 1000-4000 |
| C10 | mitosis inhibitors | | | 375-3000 |
| | | dinitroanilines | | 375-3000 |
| | | | pendimethalin | 375-3000 |
| C11 | protoporphyrinogen IX oxidase inhibitors | | | 0.5-600 |
| | | diphenyl ethers | | 50-300 |
| | | | acifluorfen | 50-300 |
| | | | acifluorfen-sodium | 50-300 |
| | | oxadiazoles | | 50-600 |
| | | | oxadiargyl | 50-600 |
| | | cyclic imides | | 0.5-300 |
| | | | carfentrazone-ethyl | 0.5-35 |
| | | | cinidon-ethyl | 3-35 |
| | | | flumiclorac-pentyl | 3-35 |
| | | | butafenacil | 5-300 |
| | | | JV 485 | 50-300 |
| C12 | photosynthesis inhibitors | | | 15-4000 |
| | | — | pyridate | 30-1500 |
| | | — | pyridafol | 30-1000 |
| | | benzothiadiazinones | | 30-1440 |
| | | | bentazone | 30-1440 |
| | | dipyridylenes | | 100-800 |
| | | | paraquat-dichloride | 100-800 |
| | | ureas | | 250-1600 |
| | | | diuron | 250-1600 |
| | | | isoproturon | 250-1600 |
| | | phenols | | 100-700 |
| | | | bromoxynil | 100-700 |
| | | chloridazon | | 500-4000 |
| | | triazines | | 15-4000 |
| | | | atrazine | 15-4000 |
| | | | terbutylazine | 250-4000 |
| | | triazinone | | 30-300 |
| | | | metribuzin | 30-300 |

TABLE 2-continued

| Component C | Class of active ingredient | Active ingredient | Rate of application (g/ha) |
|---|---|---|---|
| C13 synergists | | | 500-1500 |
| | oxiranes | | 500-1500 |
| | | tridiphane | 500-1500 |
| C14 growth substances | | | 25-1200 |
| | aryloxyalkanoic acids | | 50-1200 |
| | | fluoroxypyr | 50-400 |
| | | MCPA | 400-1200 |
| | | mecoprop-P | 400-1200 |
| | benzoic acids | | 75-800 |
| | | dicamba | 75-800 |
| | quinolinecarboxylic acids | | 25-600 |
| | | quinclorac | 25-600 |
| C16 various other herbicides | — | triaziflam | 50-750 |

[a] If appropriate, 10-50 g/ha cloquintocet may also be added.

The preferred rate of application of the safener D is 0.1 to 500 g/ha. As a rule the application rate for isoxadifen is from 0.5 to 50 g/ha, for mefenpyr from 2 to 100 g/ha and for fenchlorazol from 2 to 100 g/ha.

USE EXAMPLES

The mixtures according to the invention were applied pre- and/or post-emergence (foliar treatment). The herbicidal compounds of component B) and, if desired, of component C) as well as the safener D) were applied in the formulation in which they are present as commercially available product (s).

The herbicidally active compounds of components A), B) and, if desired, C), and, if desired D), were applied in succession or jointly, in the latter case in some cases as a tank mix and in some cases as a readymix, in the form of emulsions, aqueous solutions or suspensions, the vehicle being water (300-400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate, the action of the herbicidal compositions which can be used according to the invention, without excluding the possibility of other uses.

In these examples, the value B at which only an additive effect of the individual active ingredients is to be expected was calculated by the method of S. R. Colby (Calculating synergistic and antagonistic responses of herbicide combinations, Weeds 15, 20 pp (1967)).

This was done using the formula $$E = X + Y - \frac{XY}{100}$$

where
X=Percentage of the herbicidal action of component A) at an application rate of a;
Y=Percentage of the herbicidal action of component B), and, if desired, C), and, if desired, D) at an application rate of b, and, if desired, c, and, if desired, d;
E=expected herbicidal action of component A)+B), and, if desired C), and; if desired, D) at rates of application a+b, and, if desired, c and, if desired, d (in %).

If the value observed exceeds the value E calculated in accordance with Colby's formula, then synergism is present.

The herbicidal mixtures according to the invention exert a greater herbicidal action than would have been expected according to Colby on the basis of the observed effects of the individual components when used alone.

The results of the tests are shown in Tables 3 to 15 below. In these studies, the following plants were used:

| Scientific name | Common name |
|---|---|
| *Abutilon theophrasti* | Velvetleaf |
| *Amaranthus retroflexus* | Pigweed |
| *Avena fatua* | Wild oat |
| *Bidens pilosa* | Hairy beggarticks |
| *Brachiaria plantaginea* | Alexandergrass |
| *Commelina benghalensis* | Bengal Commelina |
| *Galium aparine* | Catchweed |
| *Pharbitis purpurea* | Common morningglory |
| *Polygonum persicaria* | Ladysthumb |

TABLE 3

Herbicidal action of compound 1a.29 and compound II (post-emergence treatment; greenhouse)

| | Application rate [g/ha ai] | *Avena fatua* Damage [%] | Colby Value E | *Pharbitis purpurea* Damage [%] | Colby Value E |
|---|---|---|---|---|---|
| Ia.29 | 3.91 | 50 | — | 70 | — |
| Compound II | 1.95 | 50 | — | 80 | — |
| Ia.29 + Compound II | 3.91 + 1.95 | 80 | 75 | 98 | 94 |

TABLE 4

Herbicidal action of compound 1a.29 and compound II (post-emergence treatment; greenhouse)

| | Application rate [g/ha ai] | *Avena fatua* Damage [%] | Colby Value E | *Abutilon theophrasti* Damage [%] | Colby Value E |
|---|---|---|---|---|---|
| Ia.29 | 1.95 | 25 | — | 40 | — |
| Compound II | 0.98 | 30 | — | 30 | — |
| Ia.29 + Compound II | 1.95 + 0.98 | 70 | 48 | 80 | 58 |

TABLE 5

Herbicidal action of compound 1a.29, compound II and atrazine (post-emergence treatment; field)

| | Application rate [g/ha ai] | *Commelina benghalensis* Damage [%] | Colby Value E |
|---|---|---|---|
| Ia.29 | 7.81 | 40 | — |
| Compound II + Atrazine | 3.91 + 62.5 | 60 | — |
| Ia.29 + Compound II + Atrazine | 7.81 + 3.91 + 62.5 | 85 | 76 |

TABLE 6

Herbicidal action of compound 1a.29, compound II and atrazine (post-emergence treatment; greenhouse)

| | Application rate [g/ha ai] | *Abutilon theophrasti* Damage [%] | Colby Value E | *Amaranthus retroflexus* Damage [%] | Colby Value E |
|---|---|---|---|---|---|
| Ia.29 | 3.91 | 80 | — | 60 | — |
| Compound II + Atrazine | 1.95 + 31.3 | 50 | — | 85 | — |
| Ia.29 + Compound II + Atrazine | 3.91 + 1.95 + 31.3 | 100 | 90 | 98 | 94 |

TABLE 7

Herbicidal action of compound 1a.29, compound II and atrazine (post-emergence treatment; field)

| | Application rate [g/ha ai] | *Bidens pilosa* Damage [%] | Colby Value E |
|---|---|---|---|
| Ia.29 | 3.91 | 30 | — |
| Compound II + Atrazine | 1.95 + 31.3 | 50 | — |
| Ia.29 + Compound II + Atrazine | 3.91 + 1.95 + 31.3 | 80 | 65 |

TABLE 8

Herbicidal action of compound 1a.29, compound II and atrazine (post-emergence treatment; greenhouse)

| | Application rate [g/ha ai] | *Abutilon theophrasti* Damage [%] | Colby Value E | *Amaranthus retroflexus* Damage [%] | Colby Value E |
|---|---|---|---|---|---|
| Ia.29 | 1.95 | 40 | — | 40 | — |
| Compound II + Atrazine | 0.98 + 15.6 | 25 | — | 60 | — |
| Ia.29 + Compound II + Atrazine | 1.95 + 0.98 + 15.6 | 80 | 65 | 85 | 76 |

TABLE 9

Herbicidal action of compound 1a.29, compound II and bentazone (post-emergence treatment; field)

| | Application rate [g/ha ai] | *Pharbitis purpurea* Damage [%] | Colby Value E |
|---|---|---|---|
| Ia.29 | 3.91 | 70 | — |
| Compound II + Bentazone | 1.95 + 62.5 | 60 | — |
| Ia.29 + Compound II + Bentazone | 3.91 + 1.95 + 62.5 | 98 | 88 |

TABLE 10

Herbicidal action of compound 1a.29, compound II and bentazone (post-emergence treatment; field)

| | Application rate [g/ha ai] | *Polygonum persicaria* Damage [%] | Colby Value E |
|---|---|---|---|
| Ia.29 | 1.95 | 95 | — |
| Compound II + Bentazone | 0.98 + 31.3 | 70 | — |
| Ia.29 + Compound II + Bentazone | 1.95 + 0.98 + 31.3 | 100 | 99 |

TABLE 11

Herbicidal action of compound 1a.29, compound II and bentazone (post-emergence treatment; greenhouse)

| | Application rate [g/ha ai] | *Abutilon theophrasti* Damage [%] | Colby Value E | *Galium aparine* Damage [%] | Colby Value E |
|---|---|---|---|---|---|
| Ia.29 | 7.81 | 95 | — | 30 | — |
| Compound II + Bentazone | 3.91 + 125 | 70 | — | 60 | — |
| Ia.29 + Compound II + Bentazone | 7.81 + 3.91 + 125 | 100 | 99 | 95 | 72 |

TABLE 12

Herbicidal action of compound 1a.29 and X* (post-emergence treatment; greenhouse)

| | Application rate [g/ha ai] | *Abutilon theophrasti* Damage [%] | Colby Value E | *Bidens pilosa* Damage [%] | Colby Value E |
|---|---|---|---|---|---|
| Ia.29 | 7.81 | 95 | — | 60 | — |
| X | 3.91 | 50 | — | 70 | — |
| Ia.29 + X | 7.81 + 3.91 | 100 | 98 | 95 | 88 |

TABLE 13

Herbicidal action of compound 1a.29, X* and atrazine (post-emergence treatment; field)

| | Application rate [g/ha ai] | *Bidens pilosa* Damage [%] | Colby Value E |
|---|---|---|---|
| Ia.29 | 7.81 | 60 | — |
| X + Atrazine | 3.91 + 62.5 | 80 | — |
| Ia.29 + X + Atrazine | 7.81 + 3.91 + 62.5 | 100 | 92 |

TABLE 14

Herbicidal action of compound 1a.29, X* and atrazine (post-emergence treatment; greenhouse)

| | Application rate [g/ha ai] | *Abutilon theophrasti* Damage [%] | Colby Value E | *Amaranthus retroflexus* Damage [%] | Colby Value E |
|---|---|---|---|---|---|
| Ia.29 | 3.91 | 80 | — | 60 | — |
| X + Atrazine | 1.95 + 31.3 | 40 | — | 85 | — |
| Ia.29 + X + Atrazine | 3.91 + 1.95 + 31.3 | 95 | 88 | 98 | 94 |

TABLE 15

Herbicidal action of compound 1a.29, X* and atrazine (post-emergence treatment; field)

| | Application rate [g/ha ai] | *Brachiaria plantaginea* Damage [%] | Colby Value E |
|---|---|---|---|
| Ia.29 | 3.91 | 80 | — |
| X + Atrazine | 1.95 + 31.3 | 70 | — |
| Ia.29 + X + Atrazine | 3.91 + 1.95 + 31.3 | 100 | 94 |

X* mixture of compound II, iodosulfuron and isoxadifen in a weigh ratio of 30:1:30 (= MaisTer®)

We claim:

1. A synergistic herbicidal mixture comprising
   A) 4-[2-methyl-3-(4,5-dihydroisoxazol-3-yl)-4-methylsulfonyl-benzoyl]-1-methyl-5-hydroxy-1H-pyrazole or one of its environmentally compatible salts; and
   B) a synergistically effective amount of the compound of formula II

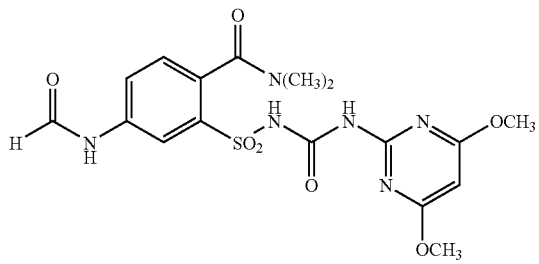

or one of its environmentally compatible salts.

2. A synergistic herbicidal mixture as claimed in claim 1, further comprising component C C) at least one herbicidal compound from the group consisting of sulfonylurea, bentazone and triazine, wherein said sulfonylurea is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, triflusulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)-benzenesulfonamide, sulfosulfuron or iodosulfuron and said triazine is selected from the group consisting of ametryn, atrazine, cyanazine, desmetryn, dimethamethryn, prometon, prometryn, propazine, simazine, simetryn, terbumeton, terbutryn, terbutylazine and trietazine.

3. A synergistic herbicidal mixture as claimed in claim 1 comprising, as component C), a sulfonylurea 4. A synergistic herbicidal mixture as claimed in claim 2 comprising, as component C), a triazine or bentazone 5. A synergistic herbicidal mixture as claimed in claim 2 comprising, as component C), a triazine 6. A synergistic herbicidal mixture as claimed in claim 2, comprising, as component C), atrazine.

7. A synergistic herbicidal mixture as claimed in claim 2, comprising, as component C), bentazone.

8. A synergistic herbicidal mixture as claimed in claim 1, further comprising isoxadifen as component D 9. A synergistic herbicidal mixture as claimed in claim 8, further comprising, as component C,
   C) one herbicidal compound from the group consisting of sulfonylurea, bentazone and triazine, wherein said sulfonylurea is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methtyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)-benzenesulfonamide, sulfosulfuron or iodosulfuron and said triazine is selected from the group consisting of ametryn, atrazine, cyanazine, desmetryn, dimethamethryn, prometon, prometryn, propazine, simazine, simetryn, terbumeton, terbutryn, terbutylazine and trietazine, 10. A synergistic herbicidal mixture as claimed in claim 2, wherein component A) and component C) are present in a weight ratio of 1:0.002 to 1:800.

11. A synergistic herbicidal mixture as claimed in claim 8, wherein component A) and component D) are present in a weight ratio of 1:0.002 to 1:800.

12. A synergistic herbicidal mixture comprising
   A) 4-[2-methyl-3-(4,5-dihydroisoxazol-3-yl)-4-methylsulfonyl-benzoyl]-1-methyl-5-hydroxy-1H-pyrazole or one of its environmentally compatible salts;
   or one of its environmentally compatible salts;
   and
   B) a synergistically effective amount of the compound of formula II

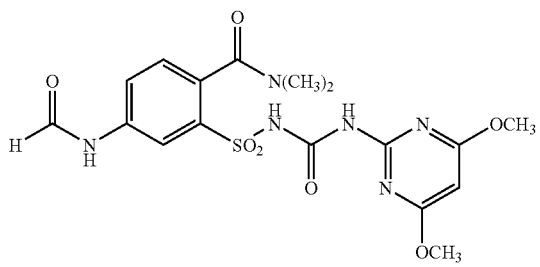

II or one of its environmentally compatible salts;
   C) at least one herbicidal compound from the group consisting of sulfonylurea, bentazone and triazine, wherein said sulfonylurea is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)-benzenesulfonamide, sulfosulfuron or iodosulfuron and said triazine is selected from the group consisting of ametryn, atrazine, cyanazine, desmetryn, dimethamethryn, prometon, prometryn, propazine, simazine, simetryn, terbumeton, terbutryn, terbutylazine and trietazine
and
   D) a safening effective amount of isoxadifen;
or an environmentally compatible salt or ester thereof.

13. A herbicidal composition comprising a herbicidally active amount of a synergistic herbicidal mixture of claim 12, and at least one inert liquid and/or solid carrier therefor.

14. A process for preparing a herbicidal composition of claim 13, comprising mixing together component A) component B) if desired, component C) if desired, component D), and at least one inert liquid and/or solid carrier therefor.

15. A method of controlling undesired vegetation, comprising applying simultaneously or separately to said vegetation, the environment of said vegetation and/or seeds of said vegetation
   A) 4-[2-methyl-3-(4,5-dihydroisoxazol-3-yl)-4-methylsulfonyl-benzoyl]-1-methyl-5-hydroxy-1H-pyrazole.
   or one of its environmentally compatible salts; and
   B) a synergistically effective amount of the compound of formula II

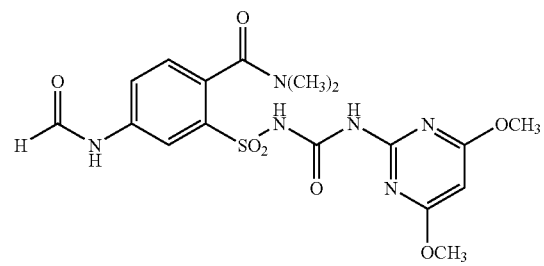

II or one of its environmentally compatible salts.

16. The method of claim 15, wherein leaves of the undesired vegetation are treated.

17. The composition of claim 13, wherein the composition further comprises at least one surfactant.

18. The method according to claim 15, further comprising components
   C) at least one herbicidal compound from the group consisting of sulfonylurea, bentazone and triazine, wherein said sulfonylurea is selected from the group consisting of amidosulfuron, azimsulfuron, bensulfuron-methyl, chlorimuron-ethyl chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)-benzenesulfonamide, sulfosulfuron or iodosulfuron and said triazine is selected from the group consisting of ametryn, atrazine, cyanazine, desmetryn, dimethamethryn, prometon, prometryn, propazine, simazine, simetryn, terbumeton, terbutryn, terbutylazine and trietazine; and D) a safening effective amount of isoxadifen or an environmentally compatible salt or ester thereof.

19. The method of claim 18, wherein at least two of component A), component B), component C), and component D) are applied in the form of a mixture.

20. The method of claim 18, wherein the components A), B), C) and D) are applied separately.

* * * * *

UNITED STATES PATENT AND TRADEMARK OFFICE
CERTIFICATE OF CORRECTION

PATENT NO. : 7,632,782 B2 Page 1 of 1
APPLICATION NO. : 10/519978
DATED : December 15, 2009
INVENTOR(S) : O'Neal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 850 days.

Signed and Sealed this

Second Day of November, 2010

David J. Kappos
*Director of the United States Patent and Trademark Office*